United States Patent [19]

Rhoades, Jr. et al.

[11] Patent Number: 5,731,210
[45] Date of Patent: Mar. 24, 1998

[54] ENVIRONMENTAL EVAPORATION CHAMBER AND METHOD OF USING SAME

[75] Inventors: Charles Bradford Rhoades, Jr., Clemmons; Ralph Thomas White, Jr., Pfafftown, both of N.C.

[73] Assignee: R. J. Reynolds Tobacco Company, Winston-Salem, N.C.

[21] Appl. No.: 810,103

[22] Filed: Feb. 25, 1997

Related U.S. Application Data

[63] Continuation of Ser. No. 572,258, Dec. 13, 1995, abandoned.

[51] Int. Cl.$^6$ .............................. C12M 1/22; B01L 3/00; B01D 1/00
[52] U.S. Cl. .................. 436/177; 159/32; 34/218; 34/232; 422/99; 422/102; 435/288.3; 435/305.1; 435/305.4
[58] Field of Search .................. 34/203, 218, 227, 34/231, 232; 422/99, 102; 435/287.1, 288.3, 288.4, 288.5, 303.1, 304.1, 304.2, 305.1, 305.2, 305.3, 305.4; 436/177, 178; 159/32

[56] References Cited

U.S. PATENT DOCUMENTS

| | | |
|---|---|---|
| 180,962 | 8/1876 | Timby . |
| 438,787 | 10/1890 | Wheeler . |
| 2,144,255 | 1/1939 | Carpenter .......................... 435/305.1 |
| 2,971,892 | 2/1961 | Carski .............................. 435/305.4 |
| 3,001,914 | 9/1961 | Andersen ........................ 435/288.3 X |
| 3,097,070 | 7/1963 | Aldrich et al. . |
| 3,127,300 | 3/1964 | Maggio ............................ 159/32 |
| 3,203,870 | 8/1965 | Andelin ........................... 435/305.4 |
| 3,288,566 | 11/1966 | Turk ................................ 422/102 |
| 3,511,298 | 5/1970 | McConnell et al. . |
| 3,684,660 | 8/1972 | Kereluk et al. .................. 435/305.1 |
| 4,008,388 | 2/1977 | McLafferty et al. . |
| 4,014,658 | 3/1977 | Arendsen et al. . |
| 4,675,298 | 6/1987 | Brüsewitz ........................ 422/102 X |
| 5,100,623 | 3/1992 | Friswell . |
| 5,270,010 | 12/1993 | Lautenschläger . |
| 5,338,409 | 8/1994 | Heierli . |

FOREIGN PATENT DOCUMENTS

2123782  9/1972  France .

OTHER PUBLICATIONS

Publication entitled *Mass Spectrometric Determination of Lead in Manganese Nodules* by T. Chow and C. McKinney, published by Analytical Chemistry, vol. 30, No. 9, Sep. 1958, pp. 1499–1503.

Publication entitled *Production and Analysis of special High–Purity Acids Purified by Sub–Boiling Distillation* by E. Kuehner et al, published by Analytical Chemistry, vol. 44, No. 12, Oct. 1972, pp. 2050–2056.

Front page, p. 273 of Table of Contents and pp. 278–281 (by Ralph E. Thiers et al.) of publication entitled *Methods of Biochemical Analysis*, vol. V, published by Interscience Publishers Ltd., London.

Publication entitled *The Role of the Analytical Blank in Accurate Trace Analysis*, by Thomas J. Purphy, published by National Bureau of Standards Special Publication 422, Issued Aug. 1976, pp. 509–539.

*Primary Examiner*—Arlen Soderquist

[57] ABSTRACT

An environmental evaporation chamber for preparing analytical samples is constructed of a plurality of separable, preferably glass, components especially designed for ease of use and low-cost manufacture. The chamber comprises an open-ended cylindrical body portion with a plurality of legs on one end thereof, a bottom tray on which the body portion is placed with the legs resting thereon to provide a gap for the exhaust of a purge gas, and a top cover which fits snugly on the upper edge of the body portion. A purge gas is introduced via a gas inlet adjacent the upper edge of the body portion and flows therethrough and exits through the gap at the lower edge of the body portion. A sample support may be provided in the body portion to raise the height of the sample into closer proximity to a heating element disposed above the top cover. A method of using the evaporation chamber involves removal and replacement of only the top cover component without the need to move the other components.

36 Claims, 2 Drawing Sheets

ENVIRONMENTAL EVAPORATION CHAMBER AND METHOD OF USING SAME

This is a continuation of application Ser. No. 08/572,258, filed on Dec. 13, 1995, now abandoned.

FIELD OF THE INVENTION

The present invention relates to laboratory glassware, in particular to a sample evaporation chamber for the evaporation of liquids from solids wherein the sample is protected from contamination by the surrounding environment and to a method of using the chamber for evaporation of liquids, such as a solvent in an analytical sample.

BACKGROUND OF THE INVENTION

A common problem in trace microanalytical analysis has been the contamination of the analytical samples by airborne particles in the laboratory. In an effort to control contamination by airborne particles, laboratories have resorted to the use of clean rooms with filtered air and evaporation chambers, either within the clean room or outside the clean room.

Evaporation chambers for the evaporation of solvents from an analytical sample have been described by Thomas J. Murphy in "The Role of the Analytical Blank in Accurate Trace Analysis," *Accuracy in Trace Analysis: Sampling Handling and Analysis*, Proceedings of the 7th IMR Symposium, pp 509–539 (1976); and by Ralph E. Thiess in "Contamination in Trace Element Analysis and its Control," *Methods of Biochemical Analysis* Vol. 5, pp 273–281 (David Girl Ed.), both of which articles are incorporated herein by reference. Those articles describe a variety of different evaporation chambers. A common problem with the evaporation chambers of the prior art has been that the environmental chambers have been cumbersome, modular in design and difficult to use with samples. Another problem has been that the modular design of the typical prior art chambers necessitates replacement of the entire apparatus when the evaporation chamber or a part of it is broken.

It would be desirable therefore to overcome those problems with the prior art devices by providing an environmental evaporation chamber that is easily manipulated in use and has parts that are relatively inexpensive to replace.

SUMMARY AND OBJECTS OF THE INVENTION

The present invention relates to evaporation chambers for the preparation of samples for chemical microanalysis and a method of using such chambers for the preparation of samples for trace level microanalysis. A primary objective of the invention is to provide an easily manipulated and operated evaporation chamber that protects an analytical sample from particulate contamination during rapid evaporation of the solvent containing the sample.

Another object of the invention is to provide a multi-piece evaporation chamber with individual pieces that may be inexpensively replaced in the event of breakage of an individual piece.

Another object of the invention is to provide an evaporation chamber with a removable top cover to allow for the easy placement in the chamber of an evaporation dish containing the sample to be dried.

Still another object of the invention is to provide an evaporation chamber with a sample evaporation dish support.

Yet another object of the invention is to provide an evaporation chamber with a bottom tray having a raised lip to retain any spills that may occur.

Another object of the invention is to provide an evaporation chamber that allows the smooth flow of gas so that a light, fluffy sample will not be disturbed by the gas flow.

The environmental chamber apparatus according to the invention is a three component device preferably made of glass, such as borosilicate glass or quartz glass. The device comprises a top cover, an open-ended chamber body portion and a bottom tray. The top cover has a substantially planar surface which fits snugly on the upper edge of the chamber body and is further provided with a downturned lip to prevent intrusion of external contamination and dislodgement of the top cover. The bottom tray supports the chamber body and top cover on a substantially planar surface and has an upturned lip that will contain any sample spills and provide a U-turn flow path for purge gas introduced into the chamber. The chamber body has a plurality of legs or standoffs extending from the lower edge thereof to provide a space or gap between the lower chamber edge and the upper surface of the bottom tray through which the purge gas introduced into the chamber can exhaust. A ribbed gas inlet tube is provided in the wall of the chamber adjacent the upper edge thereof for the introduction of a purge gas.

While the components of the present invention are shown and described as being cylindrical or circular, it will be understood that the components may have other cross-sectional shapes, such as square or rectangular. The construction of the chamber in three cylindrical/circular component parts results in a device that is especially versatile and relatively easy to manufacture and inexpensive to replace when one or more of the components is broken.

The chamber is suitable for use in laboratory microwave ovens, with hot plates or with heat lamps for drying/evaporating the solvent in an analytical sample. A sample support device, also preferably made of glass and having a diameter smaller than the chamber diameter, may be provided for use inside the chamber in a position resting on the bottom tray to decrease the distance between the sample dish and a heat lamp directed at the sample through the top cover. Support devices of various heights may be provided to accommodate different sized sample dishes. Preferably, the top cover is relatively thin to accelerate heating of the sample by an external heat lamp. If desired, the top cover may be constructed to contain a quartz heating element which would be used to supply the heat for evaporation of the solvent in the sample.

With the foregoing and other objects, advantages and features of the invention that will become hereinafter apparent, the nature of the invention may be more clearly understood by reference to the following detailed description of the invention, the appended claims and to the several views illustrated in the drawings.

DETAILED DESCRIPTION OF THE INVENTION

Figure 1:
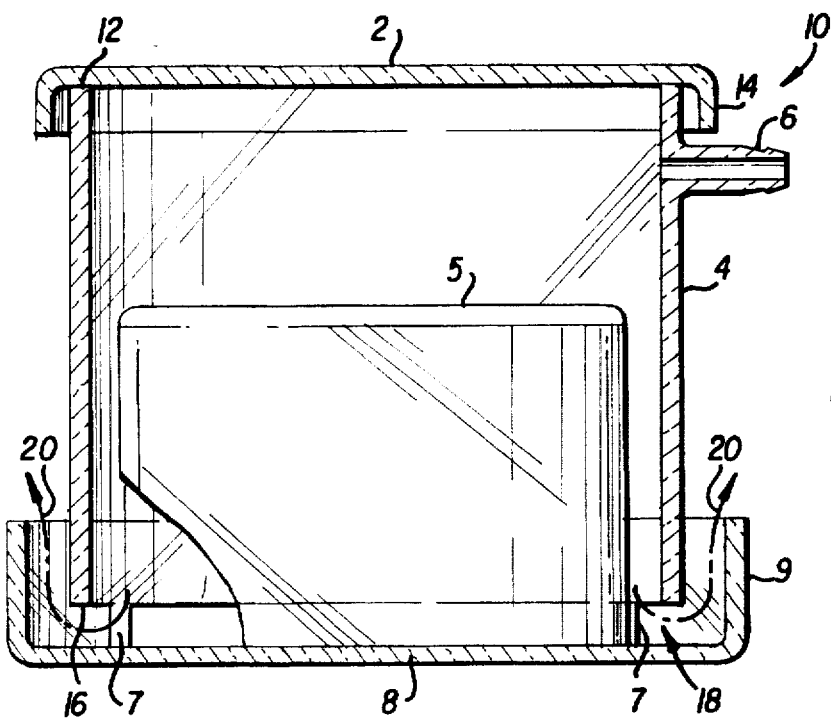
FIG. 1 is a cross-sectional view, partly broken, showing the components of the evaporation chamber of the invention.
Figure 2:
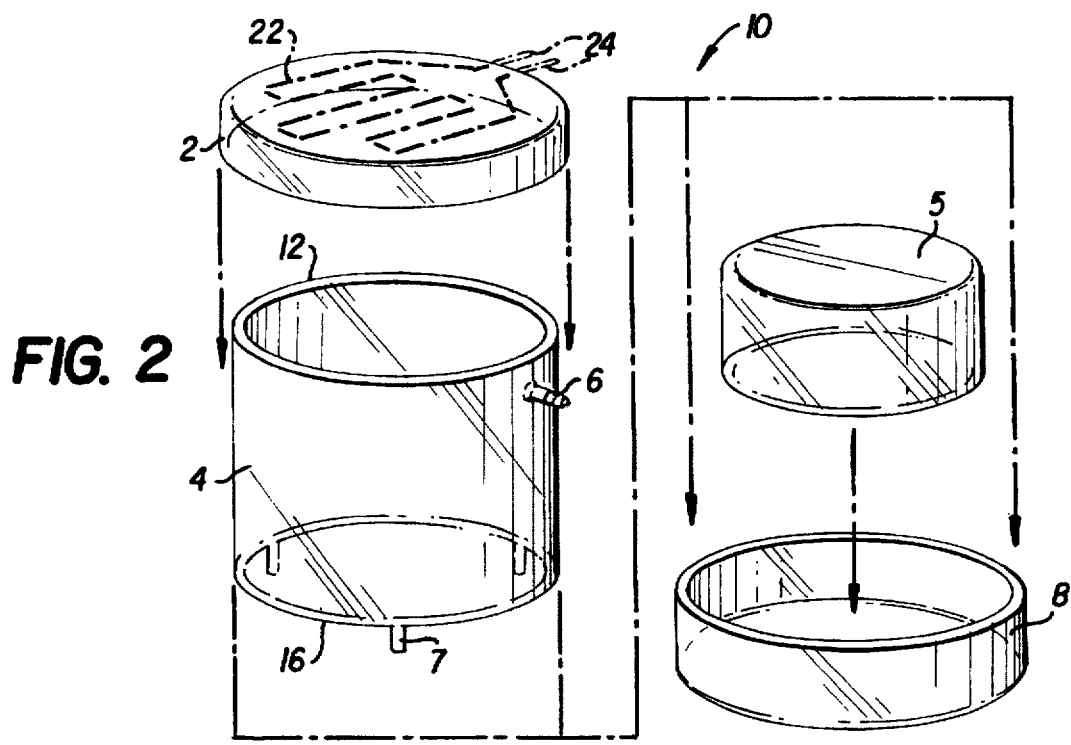
FIG. 2 is an exploded perspective view of the evaporation chamber of the invention.

Referring now to the drawings and in particular to FIGS. 1 and 2, it can be seen that the evaporation chamber of the invention, which is designated generally by reference numeral 10, comprises three major parts: a top cover 2, an open-ended chamber body portion 4 with a gas inlet tube 6 adjacent the upper end thereof, legs 7, and a bottom tray 8 with an upturned lip 9. A sample support 5 may also be provided as described in more detail hereinafter.

The top cover 2 of the evaporation chamber 10 is designed to rest snugly on the upper edge 12 of the body portion 4 of the evaporation chamber 10 with a substantially airtight fit. The top cover 2 has a downturned lip 14 that inhibits intrusion of contamination and prevents the top cover from being dislodged from the upper edge 12 of the chamber body portion 4. The body portion 4 rests on the legs 7 within the bottom tray 8 so that the lower edge 16 of the body portion 4 is spaced uniformly above the upper surface of the bottom tray 8 thereby forming an annular gap or space 18.

The diameter of the bottom tray 8 and its upturned lip 9 is greater than the diameter of the body portion 4 so that a generally U-shaped flow path shown by arrows 20 is created from the interior of the body portion 4 through the gap or space 18 between the bottom tray 8 and the body portion 4 to the exterior of the chamber. Although three equi-angularly spaced legs 7 are shown, a greater number of legs may be used to support the body portion on the bottom tray. Similarly, although the sample support 5 is shown as an inverted cylindrical glass cup, any suitable means for supporting the sample, such as a block or scissors jack can be used.

Purge gas is introduced into the chamber body portion 4 via gas inlet 6 at an adjustable flow rate up to about 40 liters/min. and passes through the chamber body portion from top to bottom carrying with it the evaporated solvent from a sample that may be contained in a sample dish (not shown) resting on sample support 5 (FIG. 1).

As shown in FIG. 2, the top cover 2 may be provided with a quartz heating element 22 attached to or formed with the glass of the top cover. Heating element 22 is provided with electrical leads 24 to which an energizing current source (not shown) may be connected.

Although the invention is not intended to be limited thereby, a suitable evaporation chamber made according to the invention has the following dimensions:

Top cover 2—borosilicate glass having a downturned lip 14 with a height of about 12 mm to 25 mm and an inside lip diameter of about 185 mm.

Chamber body 4—borosilicate glass having an outside diameter of about 178 mm, a height of about 165 mm with three legs 7 each about 12 mm long and a ¼ inch diameter ribbed gas inlet tube 6.

Bottom tray 8—borosilicate glass have an upturned lip 9 with a height of about 35 mm and an inside lip diameter of about 190 mm to 200 mm. Preferably, the diametrical dimensions of the three components are select from off-the-shelf sizes of borosilicate glass tubing or pipe.

Figure 3:
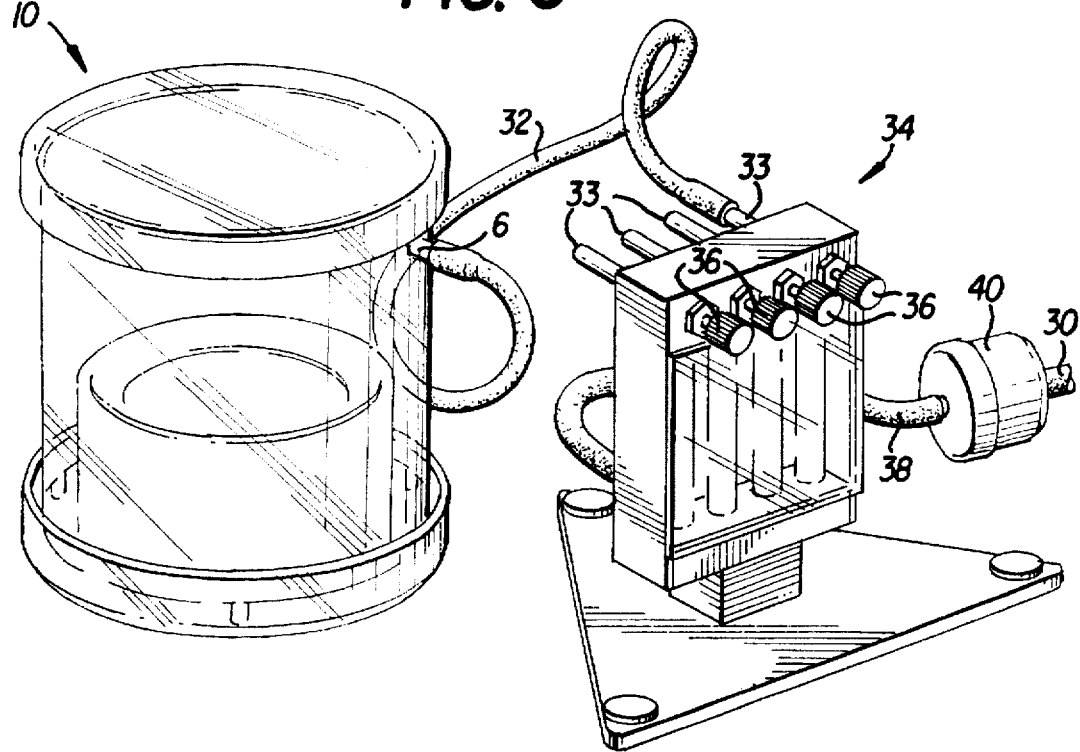
FIG. 3 is a perspective view of the evaporation chamber of the invention connected to a multiport, needle valve gas regulator and an inline gas filter.

Referring now to FIG. 3, the environmental chamber 10 is shown connected to a low pressure purge gas line 30. The connection is made between the line 30 and the gas inlet 6 of the body portion 4 as follows: Polytetrafluoroethylene tubing 32 is connected to one port 33 of a multi-port (four ports) gas regulator 34 having manually regulated needle valves 36. A gas regulator is connected, in turn, via polytetrafluoroethylene tubing 38, which may be corrugated for flexibility to a high-efficiency filter 40 connected to line 30. Other chambers 10 may be connected to the remaining ports 33 of the gas regulator 34 so that purge gas flow to each chamber may be independently regulated.

Figure 4:
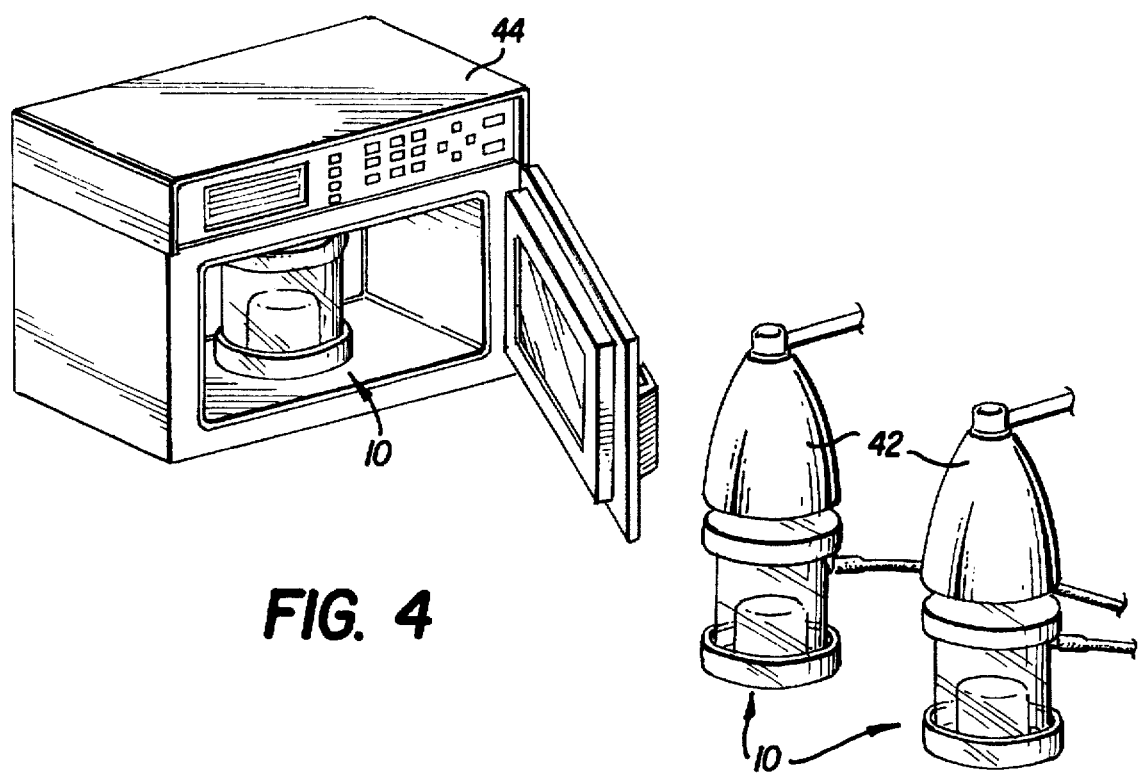
FIG. 4 is a perspective view of a plurality of evaporation chambers made according to the invention and being heated with heat lamps and in a microwave oven.

FIG. 4 illustrates the use of conventional infrared heat lamps 42 and a laboratory microwave oven 44 for heating samples in the evaporation chamber 10.

The evaporation chamber can be made of any suitable material, including polymeric materials, but is normally made of borosilicate glass. Quartz and polytetrafluoroethylene are preferred materials for certain special applications. Polytetrafluoroethylene is preferred for samples containing HF acid, and quartz is preferred for samples containing materials that would etch borosilicate glass or be contaminated by borosilicate glass.

The environmental evaporation chamber of the invention is operated as follows: The top cover 2 is removed and a sample to be dried is placed within the chamber on the sample support 5. The top cover is replaced and the filtered purge gas is flowed through the gas inlet 6 from gas line 30. The gas flow is regulated by the needle valve 36 of gas regulator 34. The sample is heated either by heat lamps 42, the heating element 22 located in the top cover, or in the microwave oven 44. A particular advantage of the present design is that the gas flow within the chamber is introduced at the top of the chamber and smoothly flows over the sample and out the bottom of the evaporation chamber. The smooth air flow is an advantage because the smooth air flow will not disturb the sample as the sample dries, especially in the case of low density samples. However, if heavy samples are to be dried, it would be preferable to place baffles within the evaporation chamber to create turbulent gas flow which will dry the sample more rapidly. If desired, the gas inlet can be positioned with its axis tangential relative to the cylindrical interior surface of the body portion or any angle between the tangent and a diametrical axis.

A particular advantage of the environmental evaporation chamber of the invention is the fact that the method of using the chamber is substantially simplified over the prior art methods. In the case of the invention, only the relatively small, lightweight top cover 2 need be removed to place a sample on the sample support 5 or retrieve it, thus facilitating the evaporation of many samples rapidly and reducing the chance of breakage of the other chamber components.

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

We claim:

1. An evaporation chamber comprising an open-ended body portion having a wall with upper and lower edges, a purge gas inlet extending through said wall and a plurality of legs connected to said wall adjacent the lower edge thereof, a top cover separable from said body portion and having a downturned lip, said top cover being adapted to rest snugly on the upper edge of said wall and a bottom tray separable from said body portion and having an upturned lip, said bottom tray being adapted to support the body portion and top cover with the legs of said body portion resting on the bottom tray, said legs forming a gap between the bottom tray and the lower edge of said body portion through which a purge gas is exhausted from the body portion.

2. The evaporation chamber of claim 1, wherein said body portion, top cover and bottom tray are made of a material selected from the group consisting of borosilicate glass, quartz glass and polytetrafluoroethylene.

3. The evaporation chamber of claim 1, wherein said body portion, top cover and bottom tray are cylindrical/circular in shape.

4. The evaporation chamber of claim 1, further comprising a sample support adapted to rest on the bottom tray inside said body portion for supporting a sample dish.

5. The evaporation chamber of claim 4, wherein said sample support is a borosilicate cylindrical glass cup having a bottom and an open end, the open end of said cup adapted to rest on the bottom tray.

6. The evaporation chamber of claim 1, including a heating element mounted to said top cover.

7. The evaporation chamber of claim 6, wherein said top cover is made of glass, said heating element comprising a quartz heating element formed in the glass of the top cover.

8. The evaporation chamber of claim 1, including a gas regulator connected by tubing to said purge gas inlet, said gas regulator having an adjustable needle valve for regulating the flow of purge gas to the chamber.

9. The evaporation chamber of claim 1 wherein said gas inlet is located adjacent the upper edge of the body portion such that purge gas flow passes through said body portion from the upper to the lower edge thereof.

10. The evaporation chamber of claim 9, wherein said gas inlet comprises a ribbed tube.

11. The evaporation chamber of claim 1, wherein one or more of said body portion, top cover or bottom tray is made of a polymeric material.

12. The evaporation chamber of claim 1, wherein said legs are integrally formed in one piece with said body portion.

13. An evaporation chamber comprising an open-ended body portion having a wall with upper and lower edges, a purge gas inlet extending through said wall and a plurality of legs connected to said wall adjacent the lower edge thereof, a top cover separable from said body portion and adapted to rest snugly on the upper edge of said wall and a bottom tray separable from said body portion and adapted to support the body portion and top cover with the legs of said body portion resting on the bottom tray, said legs forming a gap between the bottom tray and the lower edge of said body portion through which a purge gas is exhausted from the body portion.

14. The evaporation of claim 13, wherein one or more of said body portion, top cover or bottom tray is made of a polymeric material.

15. The evaporation chamber of claim 13, wherein said body portion, top cover and bottom tray are made of a material selected from borosilicate glass, quartz glass and polytetrafluoroethylene.

16. The evaporation chamber of claim 13, wherein said body portion, top cover and bottom tray are cylindrical/circular in shape.

17. The evaporation chamber of claim 13, further comprising a downturned annular lip on said top cover and an upturned annular lip on said bottom tray, the height of the annular lip on the bottom tray being greater than the height of the annular lip on the top cover.

18. The evaporation chamber of claim 13, including a heating element mounted to said top cover.

19. A method of evaporating a liquid from an analytical sample in an evaporation chamber comprising an open-ended body portion having a wall with upper and lower edges and a plurality of legs connected to said wall adjacent the lower edge thereof, a top cover separable from the body portion and a bottom tray separable from the body portion, the method comprising the steps of:

placing the bottom tray on a support;

placing the body portion on the bottom tray with the legs thereof resting on the bottom tray to form a gap between the lower edge of the body portion and the bottom tray;

placing a sample into the body portion through the upper open end thereof;

placing the top cover on the upper edge of the body portion so as to form a snug, substantially airtight interface therebetween; and introducing a purge gas into an upper part of the body portion such that the gas flows from the upper part of the body portion to a lower part thereof and exhausts through said gap with the evaporated liquid from the sample.

20. The method of claim 19, including the step of placing a sample support on the bottom tray to raise the position of the sample a predetermined height above the bottom tray and heating the sample with a heating element disposed above the sample.

21. The method of claim 19, including the step of heating the sample with a heat lamp positioned above the top cover.

22. The method of claim 19, including the step of removing the top cover after the liquid in the sample has been evaporated, placing a further sample in the body portion without moving the body portion or the bottom tray, replacing the top cover on the upper edge of the body portion and introducing a purge gas into the upper part of the body portion.

23. The method of claim 19, including heating the sample with one of a heating element disposed in the top cover, a heat lamp and a microwave oven.

24. The method of claim 19, including the step of heating the sample with microwave energy.

25. An evaporation chamber comprising an open-ended body portion having a wall with upper and lower edges, a purge gas inlet extending through said wall, a top cover separable from said body portion and adapted to rest snugly on the upper edge of said wall and a bottom tray separable from said body portion, means cooperating between said bottom tray and said body portion for supporting the body portion and top cover with a gap between the lower edge of said body portion and the bottom tray through which gap a purge gas is exhausted from the body portion.

26. The evaporation chamber of claim 25, wherein said body portion, top cover and bottom tray are made of a material selected from borosilicate glass, quartz glass and polytetrafluoroethylene.

27. The evaporation chamber of claim 25, wherein said body portion, top cover and bottom tray are cylindrical/circular in shape.

28. The evaporation chamber of claim 25, further comprising a downturned annular lip on said top cover and an upturned annular lip on said bottom tray, the height of the annular lip on the bottom tray being greater than the height of the annular lip on the top cover.

29. The evaporation chamber of claim 25, including a heating element mounted to said top cover.

30. The evaporation chamber of claim 25, wherein said supporting means comprises a plurality of legs on said body portion adjacent the lower edge thereof.

31. The evaporation chamber of claim 25, including means cooperating between said top cover and said body portion for preventing said top cover from being dislodged from the upper edge of the body portion.

32. The evaporation chamber of claim 31, wherein said preventing means comprises a downturned lip on the top cover.

33. The evaporation chamber of claim 25, wherein one or more of said body portion, top cover or bottom tray is made of a polymeric material.

34. A method of evaporating a liquid from an analytical sample in an evaporation chamber comprising an open-ended body portion having a wall with upper and lower edges, a top cover separable from the body portion and a bottom tray separable from the body portion, the method comprising the steps of:

placing the bottom tray on a support;

placing the body portion on the bottom tray with a gap between the lower edge of the body portion and the bottom tray;

placing a sample into the body portion through the upper open end thereof;

placing the top cover on the upper edge of the body portion so as to form a snug, substantially airtight interface therebetween; and introducing a purge gas into an upper part of the body portion such that the gas flows from the upper part of the body portion to a lower part thereof and exhausts through said gap with the evaporated liquid from the sample.

35. The method of claim 34, including the step of placing a sample support on the bottom tray to raise the position of the sample a predetermined height above the bottom tray and heating the sample with a heating element disposed above the sample.

36. The method of claim 34, including the step of removing the top cover after the liquid in the sample has been evaporated, placing a further sample in the body portion without moving the body portion or the bottom tray, replacing the top cover on the upper edge of the body portion and introducing a purge gas into the upper part of the body portion.

* * * * *